(12) United States Patent
Gerhardt

(10) Patent No.: US 12,402,932 B2
(45) Date of Patent: *Sep. 2, 2025

(54) PINION BLADE DRIVE MECHANISM FOR A LAPAROSCOPIC VESSEL DISSECTOR

(71) Applicant: Covidien LP, Mansfield, MA (US)

(72) Inventor: Thomas J. Gerhardt, Littleton, CO (US)

(73) Assignee: Covidien LP, Mansfield, MA (US)

( * ) Notice: Subject to any disclaimer, the term of this patent is extended or adjusted under 35 U.S.C. 154(b) by 225 days.

This patent is subject to a terminal disclaimer.

(21) Appl. No.: 18/104,345

(22) Filed: Feb. 1, 2023

(65) Prior Publication Data
US 2023/0165626 A1   Jun. 1, 2023

Related U.S. Application Data

(63) Continuation of application No. 16/390,091, filed on Apr. 22, 2019, now Pat. No. 11,576,715, which is a (Continued)

(51) Int. Cl.
| | |
|---|---|
| *A61B 18/14* | (2006.01) |
| *A61B 17/295* | (2006.01) |
| *A61B 17/29* | (2006.01) |

(52) U.S. Cl.
CPC ...... *A61B 18/1402* (2013.01); *A61B 18/1445* (2013.01); *A61B 2017/2923* (2013.01); (Continued)

(58) Field of Classification Search
CPC ................. A61L 8/1402; A61L 8/1445; A61B 2018/1412; A61B 2018/1455; A61B 17/295; A61B 2017/2923
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| | (Continued) | |

FOREIGN PATENT DOCUMENTS

| | | |
|---|---|---|
| DE | 2415263 A1 | 10/1975 |
| DE | 02514501 A1 | 10/1976 |
| | (Continued) | |

OTHER PUBLICATIONS

Michael Choti, "Abdominoperineal Resection with the LigaSure Vessel Sealing System and LigaSure Atlas 20 cm Open Instrument" Innovations That Work, Jun. 2003.

(Continued)

*Primary Examiner* — Michael F Peffley
*Assistant Examiner* — Samantha M Good

(57) ABSTRACT

A surgical instrument comprises a handle assembly including an actuator. An elongate shaft extends distally from the handle assembly and defines a longitudinal axis. A reciprocating member extends at least partially through the elongate shaft, and is mounted for longitudinal motion through the elongate shaft in response to manipulation of the actuator. A drive mechanism includes a first rotating component coupled to the actuator to induce rotational motion in the first rotating component. A second rotating component is coupled to the first rotating component such that rotational motion in the first rotating component induces rotational motion in the second rotating component. The second rotating component is coupled to the reciprocating member such that rotational motion of the second rotating component induces longitudinal motion in the reciprocating member.

20 Claims, 6 Drawing Sheets

Related U.S. Application Data continuation of application No. 12/773,644, filed on May 4, 2010, now Pat. No. 10,265,118.

(52) U.S. Cl.
CPC ..... *A61B 17/295* (2013.01); *A61B 2018/1412* (2013.01); *A61B 2018/1455* (2013.01)

(56) References Cited

U.S. PATENT DOCUMENTS

| | | | |
|---|---|---|---|
| D295,894 S | 5/1988 | Sharkany et al. | |
| 5,084,054 A | 1/1992 | Bencini et al. | |
| 5,201,743 A | 4/1993 | Haber et al. | |
| D348,930 S | 7/1994 | Olson | |
| 5,582,617 A | 12/1996 | Klieman et al. | |
| 5,597,107 A | 1/1997 | Knodel et al. | |
| 5,620,459 A | 4/1997 | Lichtman | |
| 5,653,721 A | 8/1997 | Knodel et al. | |
| D384,413 S | 9/1997 | Zlock et al. | |
| 5,662,258 A | 9/1997 | Knodel et al. | |
| 5,827,323 A | 10/1998 | Klieman et al. | |
| 5,993,467 A | 11/1999 | Yoon | |
| 6,024,741 A | 2/2000 | Williamson, IV et al. | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| 7,128,254 B2 | 10/2006 | Shelton, IV et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,500,975 B2 | 3/2009 | Cunningham et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 8,112,871 B2 | 2/2012 | Brandt et al. | |
| 8,133,254 B2 | 3/2012 | Dumbauld et al. | |
| 8,162,965 B2 | 4/2012 | Reschke et al. | |
| 8,187,273 B2 | 5/2012 | Kerr et al. | |
| 8,226,650 B2 | 7/2012 | Kerr | |
| 8,251,994 B2 | 8/2012 | McKenna et al. | |
| 8,252,626 B2 | 8/2012 | Cho et al. | |
| 8,266,783 B2 | 9/2012 | Brandt et al. | |
| 8,287,536 B2 | 10/2012 | Mueller et al. | |
| 8,292,886 B2 | 10/2012 | Kerr et al. | |
| 8,323,310 B2 | 12/2012 | Kingsley | |
| 8,343,150 B2 | 1/2013 | Artale | |
| 8,343,151 B2 | 1/2013 | Siebrecht et al. | |
| 8,357,159 B2 | 1/2013 | Romero | |
| 8,388,647 B2 | 3/2013 | Nau, Jr. et al. | |
| 8,409,246 B2 | 4/2013 | Kerr et al. | |
| 8,409,247 B2 | 4/2013 | Garrison et al. | |
| 8,425,511 B2 | 4/2013 | Olson | |
| 8,430,876 B2 | 4/2013 | Kappus et al. | |
| 8,430,877 B2 | 4/2013 | Kerr et al. | |
| 8,439,911 B2 | 5/2013 | Mueller | |
| 8,439,913 B2 | 5/2013 | Horner et al. | |
| 8,469,991 B2 | 6/2013 | Kerr | |
| 8,469,992 B2 | 6/2013 | Roy et al. | |
| 8,480,671 B2 | 7/2013 | Mueller | |
| 8,491,624 B2 | 7/2013 | Kerr et al. | |
| 8,491,625 B2 | 7/2013 | Horner | |
| 8,491,626 B2 | 7/2013 | Roy et al. | |
| 8,512,336 B2 | 8/2013 | Couture | |
| 8,512,371 B2 | 8/2013 | Kerr et al. | |
| 8,540,749 B2 | 9/2013 | Garrison et al. | |
| 8,556,929 B2 | 10/2013 | Harper et al. | |
| 8,568,397 B2 | 10/2013 | Horner et al. | |
| 8,568,412 B2 | 10/2013 | Brandt et al. | |
| 8,585,736 B2 | 11/2013 | Horner et al. | |
| 8,597,295 B2 | 12/2013 | Kerr | |
| 8,623,018 B2 | 1/2014 | Horner et al. | |
| 8,647,343 B2 | 2/2014 | Chojin et al. | |
| 10,265,118 B2 * | 4/2019 | Gerhardt | A61B 18/1445 |
| 11,576,715 B2 * | 2/2023 | Gerhardt | A61B 18/1445 |
| 2003/0018332 A1 | 1/2003 | Schmaltz et al. | |
| 2003/0114851 A1 | 6/2003 | Truckai et al. | |
| 2005/0283150 A1 | 12/2005 | Moutafis et al. | |
| 2006/0049230 A1 * | 3/2006 | Shelton | A61B 17/07207 227/19 |
| 2008/0300613 A1 | 12/2008 | Shelton, IV et al. | |
| 2010/0204697 A1 | 8/2010 | Dumbauld et al. | |
| 2010/0204698 A1 | 8/2010 | Chapman et al. | |
| 2010/0217258 A1 | 8/2010 | Floume et al. | |
| 2010/0249769 A1 | 9/2010 | Nau, Jr. et al. | |
| 2010/0274244 A1 | 10/2010 | Heard | |
| 2010/0280511 A1 | 11/2010 | Rachlin et al. | |
| 2010/0307934 A1 | 12/2010 | Chowaniec et al. | |
| 2011/0034918 A1 | 2/2011 | Reschke | |
| 2011/0046623 A1 | 2/2011 | Reschke | |
| 2011/0054468 A1 | 3/2011 | Dycus | |
| 2011/0054471 A1 | 3/2011 | Gerhardt et al. | |
| 2011/0060335 A1 | 3/2011 | Harper et al. | |
| 2011/0071523 A1 | 3/2011 | Dickhans | |
| 2011/0073594 A1 | 3/2011 | Bonn | |
| 2011/0077648 A1 | 3/2011 | Lee et al. | |
| 2011/0087208 A1 | 4/2011 | Boudreaux et al. | |
| 2011/0118736 A1 | 5/2011 | Harper et al. | |
| 2011/0190765 A1 | 8/2011 | Chojin | |
| 2011/0193608 A1 | 8/2011 | Krapohl | |
| 2011/0218530 A1 | 9/2011 | Reschke | |
| 2011/0230880 A1 | 9/2011 | Chojin et al. | |
| 2011/0251605 A1 | 10/2011 | Hoarau et al. | |
| 2011/0270245 A1 | 11/2011 | Horner et al. | |
| 2011/0270251 A1 | 11/2011 | Horner et al. | |
| 2011/0276048 A1 | 11/2011 | Kerr et al. | |
| 2011/0276049 A1 | 11/2011 | Gerhardt | |
| 2011/0295251 A1 | 12/2011 | Garrison | |
| 2011/0295313 A1 | 12/2011 | Kerr | |

FOREIGN PATENT DOCUMENTS

| | | |
|---|---|---|
| DE | 2627679 A1 | 1/1977 |
| DE | 03423356 A1 | 1/1986 |
| DE | 03612646 A1 | 4/1987 |
| DE | 3712328 A1 | 10/1988 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 202007009317 U1 | 8/2007 |
| DE | 102004026179 B4 | 1/2009 |
| EP | 1159926 A2 | 12/2001 |
| JP | 61501068 | 9/1984 |
| JP | 65502328 | 3/1992 |
| JP | 55106 | 1/1993 |
| JP | 540112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11070124 | 3/1999 |
| JP | 11244298 | 9/1999 |
| JP | 2000102545 A | 4/2000 |

(56) References Cited

FOREIGN PATENT DOCUMENTS

| JP | 2000342599 A | 12/2000 |
|---|---|---|
| JP | 2000350732 A | 12/2000 |
| JP | 2001008944 | 1/2001 |
| JP | 2001029356 | 2/2001 |
| JP | 2001128990 A | 5/2001 |
| SU | 401367 A1 | 10/1973 |
| WO | 0036986 A1 | 6/2000 |
| WO | 0154604 A1 | 8/2001 |
| WO | 2005110264 A3 | 4/2006 |

OTHER PUBLICATIONS

Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al., "Comparison of Healing Process Following Ligation with Sutures and Bipolar Vessel Sealing" Surgical Technology International (2001).
"Electrosurgery: A Historical Overview". Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan., 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Darus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/ Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" . Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/ Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase | Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, bp. 21-24.
Levy et al., "Update on Hysterectomy-New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery {2001) 71 .9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales/ Product Literature 2000.
Jarrett et al., "Use of the LigaSure Vessel Sealing System for Peri-Hilar Vessels in Laparoscopic Nephrectomy"; Sales/ Product Literature 2000.
Crouch et al. "A Velocity-Dependent Model for Needle Insertion in Soft Tissue" MICCAI 2005; LNCS 3750 pp. 624-632 Dated: 2005.
McLellan et al., "Vessel Sealing for Hemostasis During Pelvic Surgery" Int'l Federation of Gynecology and Obstetrics Figo World Congress 2000, Washington, DC.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Intl Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.

(56) References Cited

OTHER PUBLICATIONS

Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report-extended-EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

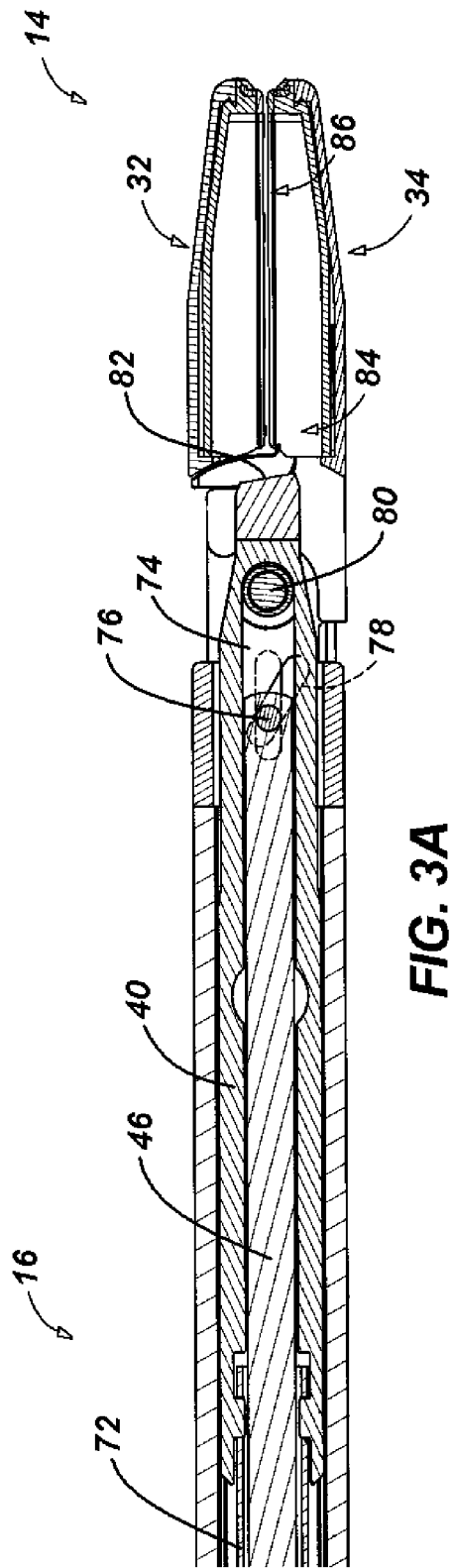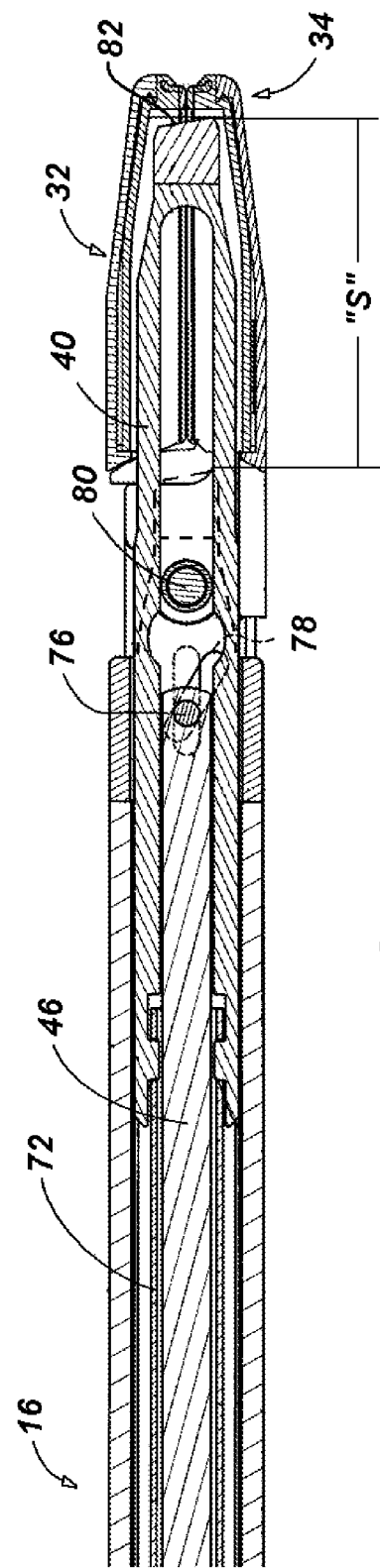

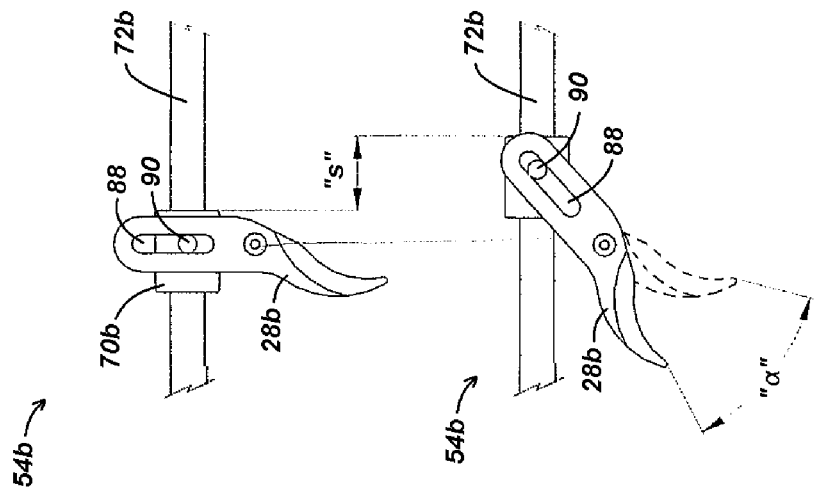
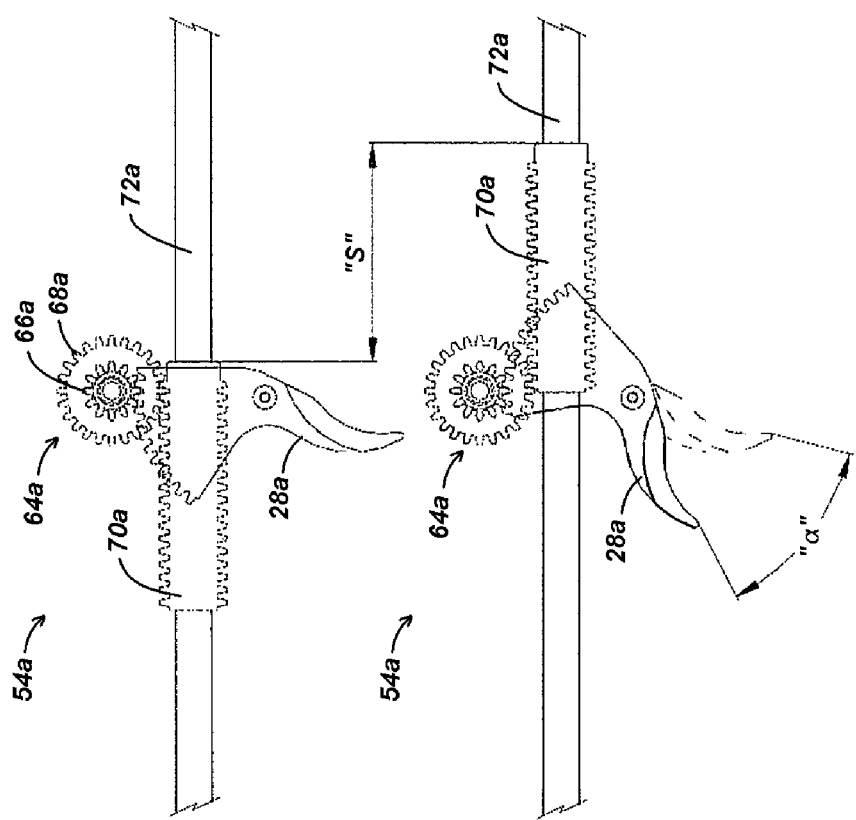

PINION BLADE DRIVE MECHANISM FOR A LAPAROSCOPIC VESSEL DISSECTOR

CROSS-REFERENCE TO RELATED APPLICATIONS

This application is a continuation of U.S. patent application Ser. No. 16/390,091, filed on Apr. 22, 2019, now U.S. Pat. No. 11,576,715, which is a continuation of U.S. patent application Ser. No. 12/773,644, filed on May 4, 2010, now U.S. Pat. No. 10,265,118.

INTRODUCTION

The present disclosure relates to an apparatus for joining and transecting tissue. In particular, the disclosure relates to an apparatus having a drive mechanism for advancing a blade through tissue.

BACKGROUND

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. To transect the tissue, an operator may squeeze a trigger or manipulate a similar actuator to advance a sharpened blade distally through a channel defined in the jaws. Since it is generally not necessary to release the tissue captured between the jaws before the blade is actuated, an accurate cut may be formed that extends only through tissue that has been properly sealed. A detailed discussion of the use of an electrosurgical forceps may be found in U.S. Pat. No. 7,255,697 to Dycus et al.

Certain surgical procedures may be performed more quickly and accurately with an electrosurgical forceps having relatively longer jaws than one having shorter jaws. To this end, electrosurgical forceps have become available with jaws 60 mm in length or more. Longer jaws, however, may tend to present difficulties in transecting the sealed tissue. Since longer jaws are associated with greater distances a blade must traverse to fully transect tissue captured between the jaws, a longer actuation stroke may be required by an operator. A longer stroke may prove to be awkward or cumbersome for an operator.

SUMMARY

The present disclosure describes a surgical instrument including a handle assembly having an actuator mounted for manipulation through an actuation stroke. An elongate shaft extends distally from the handle assembly and defines a longitudinal axis. A reciprocating member extends at least partially through the elongate shaft and is mounted for longitudinal motion through the elongate shaft. A drive mechanism is included for inducing longitudinal motion in the reciprocating member in response to manipulation of the actuator through the actuation stroke. The drive mechanism includes a first rotating component defining a first circumference, wherein the first rotating component is coupled to the actuator about the first circumference such that the manipulation of the actuator through the actuation stroke induces rotational motion in the first rotating component. The drive mechanism also includes a second rotating component defining a second circumference wherein the second rotating component is coupled to the first rotating component such that rotational motion in the first rotating component induces rotational motion in the second rotating component. The second rotating component is further coupled to the reciprocating member about the second circumference such that rotational motion of the second rotating component induces longitudinal motion in the reciprocating member. The second circumference is greater than the first circumference.

The first rotating component may include a pinion gear defining a plurality of discrete teeth engaged with the actuator. The actuator may include a trigger mounted for pivoting through an actuation stroke to define an angle. Alternatively, the first rotating component may include a pulley, which is coupled to the actuator by a belt, and the actuator may include a drive wheel mounted for rotational motion.

The second rotating component may include a gear having a plurality of discrete teeth engaged with a rack also having a plurality of discrete teeth and being mounted for longitudinal motion. Each of the plurality of discrete teeth of the rack may encircle a circumferential surface of the rack, and the rack may be mounted for rotational motion about the longitudinal axis.

The surgical instrument includes an end effector extending distally from the elongate shaft. The end effector may include a pair of jaw members wherein at least one jaw member is configured to move between an open position substantially spaced from the other of the pair of jaw members and a closed position wherein the jaw members are closer together. The reciprocating member may be coupled to a knife adjacent a distal end of the reciprocating member, and the knife may be selectively extendable through a knife channel defined in the jaw members. The jaw members may include at least one electrode connectable to a source of electrosurgical energy.

According to another aspect of the disclosure, an electrosurgical instrument includes a handle assembly including an actuator mounted for manipulation through an actuation stroke. An elongate shaft extends distally from the handle assembly and defines a longitudinal axis. An end effector extends distally from the elongate shaft. The end effector includes a pair of jaw members wherein at least one jaw member is configured to move between an open position substantially spaced from the other of the pair of jaw members and a closed position wherein the jaw members are closer together. The pair of jaw members includes at least one electrode connectable to a source of electrosurgical energy. A reciprocating member extends at least partially through the elongate shaft and is mounted for longitudinal motion through the elongate shaft. A knife is coupled to the reciprocating member and is extendable into the end effector. A drive mechanism for inducing longitudinal motion in the reciprocating member in response to manipulation of the actuator through the actuation stroke includes a gear set having a first gear engaging the actuator and a second gear engaging the reciprocating member. The gear set defines a gear ratio less than one. The gear ratio may be about 1:2.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3A is a partial, cross-sectional view of an end effector of the instrument of FIG. 1 depicting the blade in the retracted position;

FIG. 3B is a partial, cross-sectional view of the end effector of FIG. 4 depicting the blade in the advanced position;

FIG. 4 is a schematic view of a pinion drive mechanism operated through an actuation stroke defining an angle;

FIG. 5 is a schematic view of a pin-and-slot drive mechanism operated through an actuation stroke defining the same angle represented in FIG. 4.

DETAILED DESCRIPTION

Figure 1:
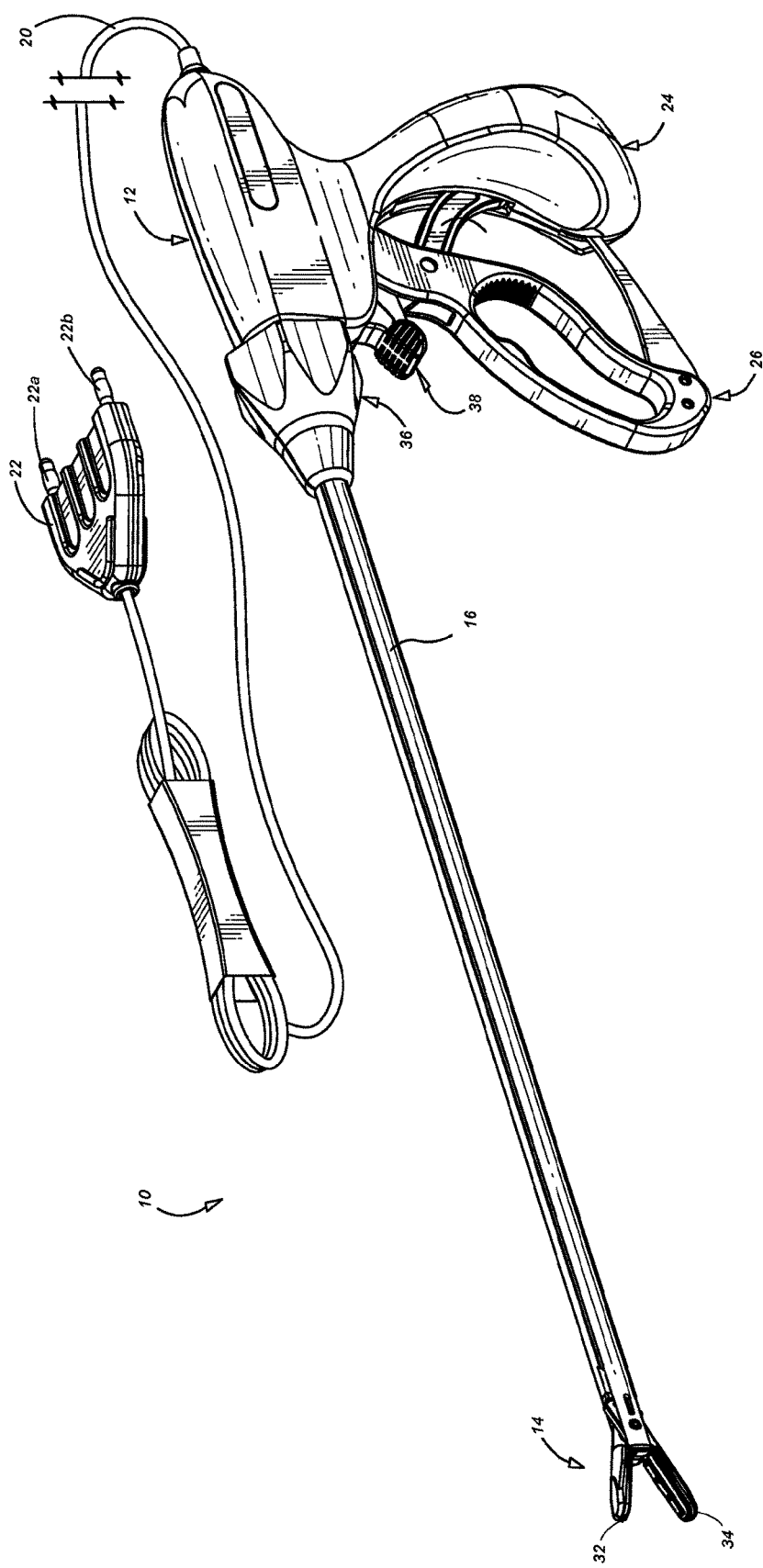
FIG. 1 is a perspective view of a surgical instrument in accordance with an embodiment of the present disclosure.

Referring initially to FIG. 1, an embodiment of an electrosurgical instrument is depicted generally as 10. The instrument 10 includes a handle assembly 12 for remotely controlling an end effector 14 through an elongate shaft 16. Although this configuration is typically associated with instruments for use in endoscopic surgical procedures, various aspects of the present disclosure may be practiced in connection with traditional open procedures as well.

Handle assembly 12 is coupled to an electrosurgical cable 20, which may be used to connect the instrument 10 to a source of electrosurgical energy. The cable 20 extends to connector 22 including prong members 22a and 22b that are dimensioned to mechanically and electrically connect the instrument 10 to an electrosurgical generator (not shown). Each of the two prong members 22a and 22b may be associated with an opposite electrical terminal or potential (supplied by the generator) such that bipolar energy may be conducted through the cable 20, and to the end effector 14. Alternatively, the instrument 10 may include a battery and/or a generator (not shown) disposed onboard the instrument 10 such that the instrument may operate as a self-contained unit.

To control the end effector 14, the handle assembly 12 includes a stationary handle 24 and movable handle 26. The movable handle 26 may be separated and approximated relative to the stationary handle 24 to respectively open and close the end effector 14. In FIG. 1, the end effector 14 is depicted in an open configuration wherein upper and lower jaw members 32 and 34 are separated from one another such that tissue may be received therebetween. The jaw members 32, 34 are pivotally coupled to the elongate shaft, and thus may be moved to a closed configuration (See FIG. 3A) wherein the jaw members 32, 34 are closer together for clamping the tissue. Any known mechanism may be incorporated into the instrument 10 to operatively couple the jaw members 32, 34 to the handle assembly 12 including those described in U.S. Pat. No. 7,101,371 to Dycus et al. Handle assembly 12 also includes a rotation knob 36, which may be manipulated to rotate the end effector 14 about a longitudinal axis A-A defined by the elongate shaft 16, and a trigger 38 which is operable to advance a blade or knife 40 (see FIG. 3A) through end effector 14 as discussed below with reference to FIGS. 2A through 3B.

Figure 2A:
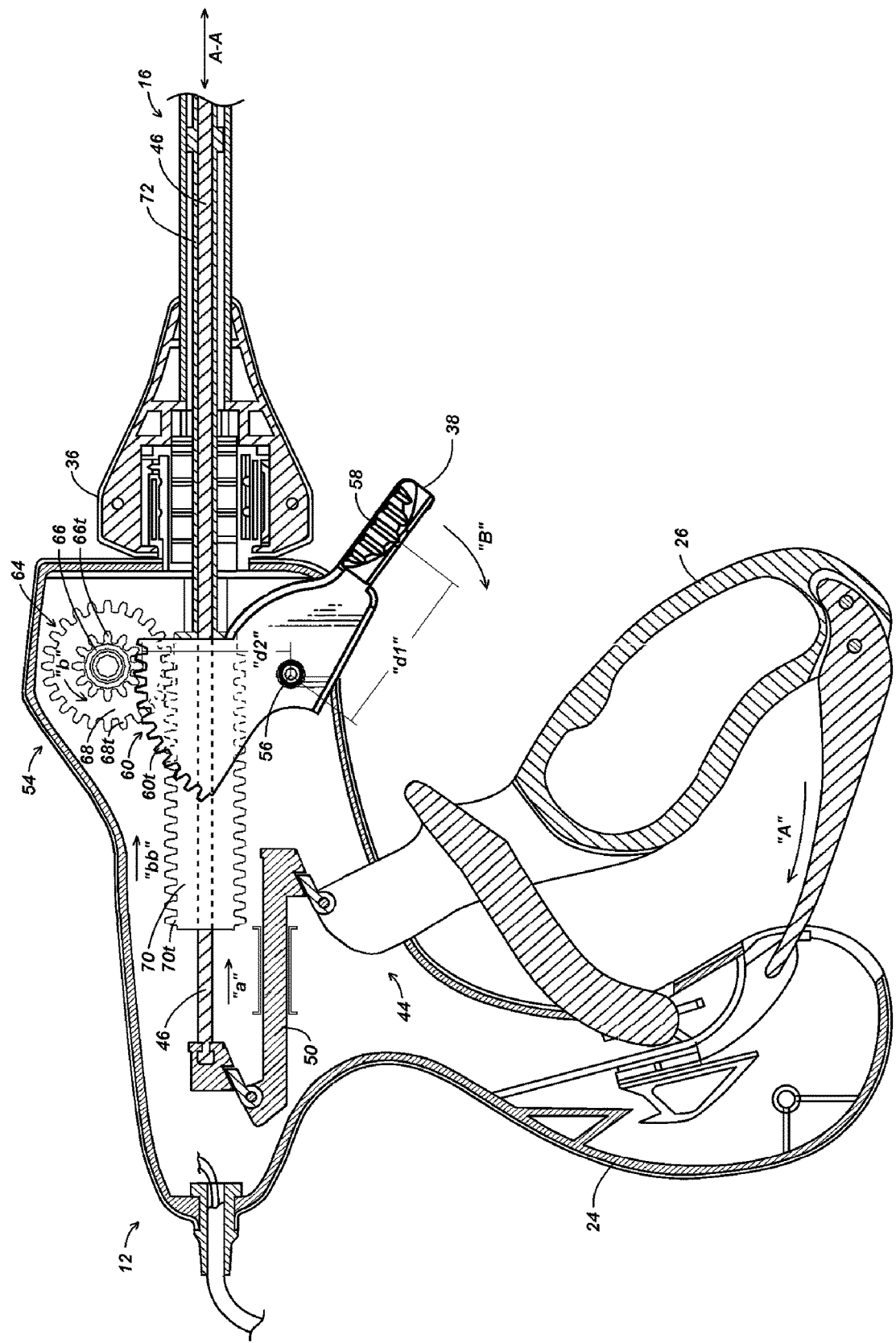
FIG. 2A is a partial, cross-sectional view of a handle assembly of the instrument of FIG. 1 depicting a trigger in an un-actuated position for maintaining a blade in a retracted position.

Referring now to FIG. 2A, a clamping mechanism 44 for closing the jaw members 32, 34 includes a drive rod 46 extending through the elongate shaft 16. The drive rod 46 is coupled at a proximal end to a coupling member 50, which is slidably disposed within the stationary handle 24. The coupling member 50 is operatively coupled to the movable handle 26 such that as the movable handle 26 is approximated with the stationary handle 24 in the direction of arrow "A," the coupling member 50 is driven distally in the direction of arrow "a." The drive rod 46 is, in turn, also driven in the direction of arrow "a" by the coupling member 50. Such longitudinal motion in drive rod 46 may effect pivotal motion in the jaw members 32, 34 as described below with reference to FIG. 3A.

A pinion drive mechanism 54 for advancing the knife 40 is also disposed in the handle assembly 24. The pinion drive mechanism 54 is operable by trigger 38, which is pivotally mounted to stationary handle 24 about pivot pin 56. Trigger 38 includes a grip 58 protruding to an exterior of the stationary handle 24 such that the grip 58 is accessible by an operator while gripping handle assembly 12. The grip 58 is disposed at a first distance "d1" from pivot pin 56. Opposite the grip 58, on an interior of the stationary handle 24, the trigger 38 includes a curved driving face 60. The driving face 60 is centered about pivot pin 56 at second distance "d2," and includes a plurality of discreet teeth 60t. The trigger 38 defines a simple lever mechanism such that, for a given force applied at the grip 58, a driving force delivered at the driving face 60 may be varied by varying the distances d1 and d2 from the pivot pin 56.

The teeth 60t of trigger 38 engage a circular gear set 64 that is rotatably coupled to the stationary handle 24. The gear set 64 includes a smaller pinion gear 66 and a larger intermediate gear 68. Although the ratio between the diameters of pinion gear 66 and intermediate gear 68 may vary, as depicted the smaller pinion gear 66 has a diameter approximately half the diameter of the larger intermediate gear 68, and thus exhibits a circumference about half the circumference of the intermediate gear 68. The gear set 64 defines a gear ratio of about 1:2, and thus, a tooth 68t on intermediate gear 68 travels approximately twice the distance as a tooth 66t on the pinion gear per rotation of the gear set 64. The teeth 66t of the pinion gear 66 engage the teeth 60t of the trigger driving face 60 while the teeth 68t of the intermediate gear 68 engage a cylindrical rack 70.

The cylindrical rack 70 is movably disposed about the drive rod 46, such that the rack 70 may translate longitudinally within the handle assembly 12. The rack 70 includes a plurality of circumferential teeth 70t encircling an outer surface thereof. The circumferential teeth 70t permit the rack 70 to maintain engagement with intermediate gear 68 regardless of the radial orientation of the rack 70 about the longitudinal axis A-A. Thus, the rack 70 is configured to rotate along with rotation knob 36. A distal end of the cylindrical rack 70 fixedly engages a knife tube 72 such that both rotational and longitudinal motion may be transferred between the knife tube 72 and the cylindrical rack 70. The knife tube 72 extends through the elongate shaft 16 such that the knife tube 72 may be coupled to knife 40 (FIG. 3A) as described in greater detail below.

Figure 2B:
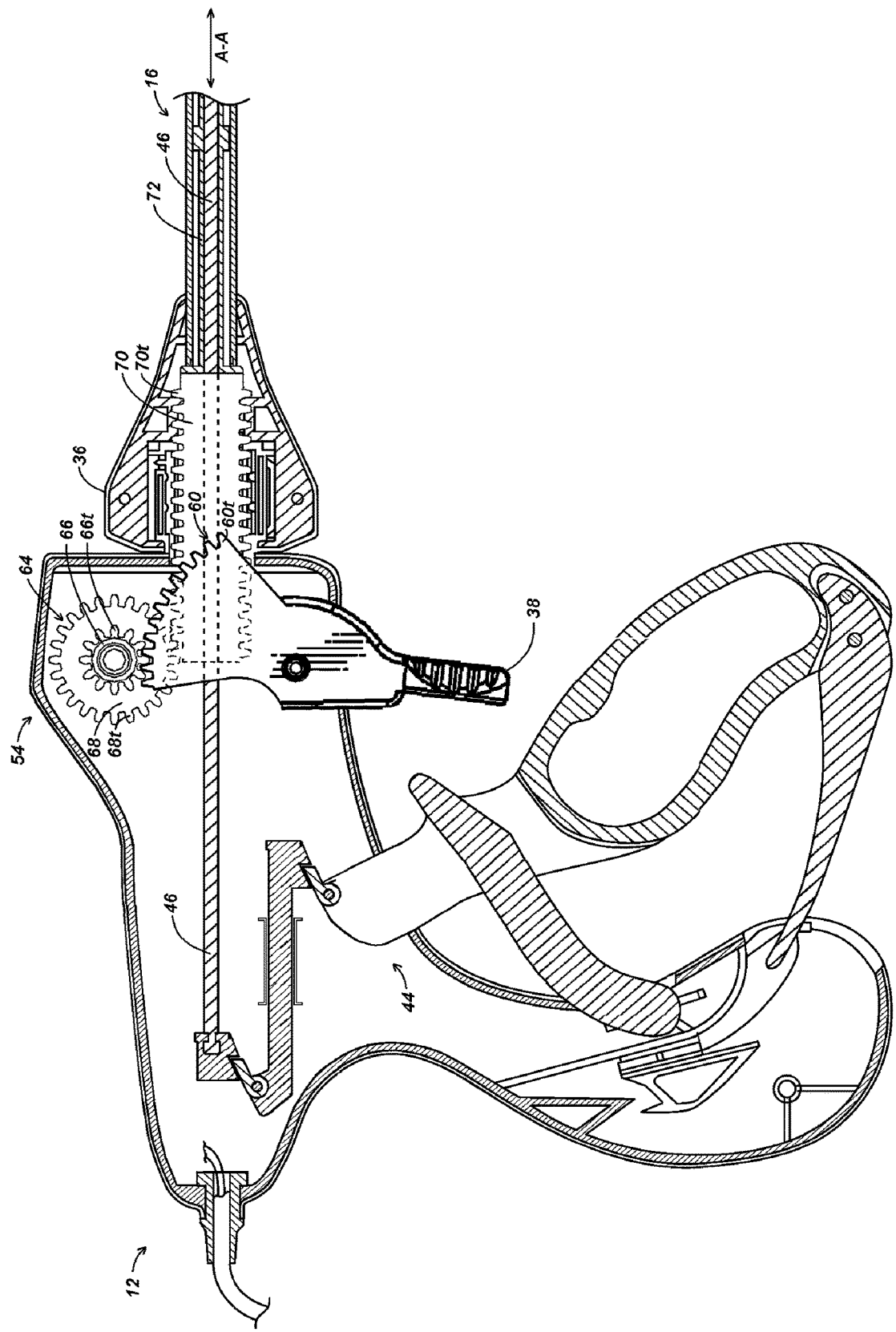
FIG. 2B is a partial, cross-sectional view of the handle assembly of FIG. 2A depicting the trigger in an actuated position for maintaining a blade in an advanced position.

In use, the trigger 38 may be moved from an un-actuated position, as depicted in FIG. 2A, in the direction of arrow "B", to an actuated position, as depicted in FIG. 2B to advance the knife tube 72 distally. As the trigger 38 rotates about pivot pin 56, the teeth 60*t* engage teeth 66*t* to drive the gear set 64 in the direction of arrow "b." The teeth 68*t* of the gear set 64, in turn, drives the cylindrical rack 70 and knife tube 72 distally in the direction of arrow "bb." The knife tube 72 may be retracted by returning the trigger 38 to the un-actuated position. The pinion drive mechanism 54 exhibits a reduction in force applied at the knife tube 72 as compared to a force applied to the trigger 38. Where greater forces are required, the trigger 72 may be modified by appropriately altering the distances "d1" and "d2."

Referring now to FIGS. 3A and 3B, the knife tube 72 is coupled to knife 40 proximate a distal end of the knife tube 72. The knife 40 is bifurcated to define a central elongate slot 74 therein. The elongate slot 74 permits longitudinal reciprocation of the drive rod 46 therethrough in response to manipulation of the movable handle 26 (FIG. 2A). The drive rod 46 is coupled to jaw members 32, 34 by a drive pin 76 extending through angled slots 78 defined in the jaw members 32, 34. The drive pin 76 reciprocates longitudinally with the drive rod 46 such that the drive pin 76 engages the angled slots 78 to cause jaw members 32, 34 to pivot about pivot pin 80, and thus moves the jaw members 32, 34 between open and closed positions.

Reciprocation of the knife tube 72 in response to manipulation of the trigger 38, induces reciprocation of the knife 40 between a retracted position as depicted in FIG. 3A, and an advanced position as depicted in FIG. 3B. The retracted position of the knife 40 corresponds to the un-actuated position of trigger 38 (FIG. 2A) and the advanced position of the knife 40 corresponds to the actuated position of the trigger (FIG. 2B). In the advanced position, a sharpened cutting edge 82 of the knife 40 extends into a knife channel 84 defined in the jaw members 32, 34. The knife channel 84 extends between laterally disposed electrodes 86 on the jaw members 32, 34, which are configured to electrosurgically seal or otherwise treat tissue. The knife 40 may thus be moved from the retracted position wherein the cutting edge 82 is proximal to the electrodes 86 to the advanced position while transecting tissue captured between the electrodes 86. The length of the jaws 32, 34 defines the knife stroke "S," or the distance the knife 40 must travel between the retracted and advanced positions, to fully transect tissues captured between the electrodes 86. The knife stroke "S," corresponds to the distance the rack 70 travels as the trigger 38 is moved between the un-actuated and actuated positions (see FIGS. 2A and 2B).

For a given actuation stroke, a pinion drive mechanism 54*a* as depicted in FIG. 4 may offer a greater knife stroke "S" than a pin-and-slot drive mechanism 54*b* as depicted in FIG. 5. The pinion drive mechanism 54*a* includes a trigger 28*a*, which is pivotable through an actuation stroke defining an angle "α". Movement of the trigger 28*a* through the actuation stroke rotates a gear set 64*a*, which in turn drives the rack 70*a* in a longitudinal direction as described above with reference to FIGS. 2A and 2B. The rack 70*a*, and thus a knife tube 72*a*, is translated through knife stroke "S."

The pin-and-slot mechanism 54*b* includes a trigger 28*b*, which is pivotable through an actuation stroke defining the same angle "α". The trigger 28*b* includes a slot 88, which engages a pin 90 of a translation block 70*b*. The translation block 70*b* is driven in a longitudinal direction as the trigger 28*b* pivots. Movement of the trigger 28*b* though the actuation stroke, however, translates the block 70*b*, by only a reduced knife stroke "s."

For components sized and positioned suitably for use in a surgical instrument, the knife stroke "S" and the reduced knife stroke "s" have been empirically determined for an actuation stroke defining an angle "α" of 47.97°. The pinion drive mechanism 54*a* yielded a knife stroke "S" of 54.6 mm while the pin-and-slot drive mechanism yielded a reduced knife stroke "s" of 19.8 mm. A pinion drive mechanism 54*a* may achieve such a knife stroke "S" when an intermediate gear 68*a* exhibits a diameter approximately twice the diameter of a pinion gear 66*a*.

Figure 6:
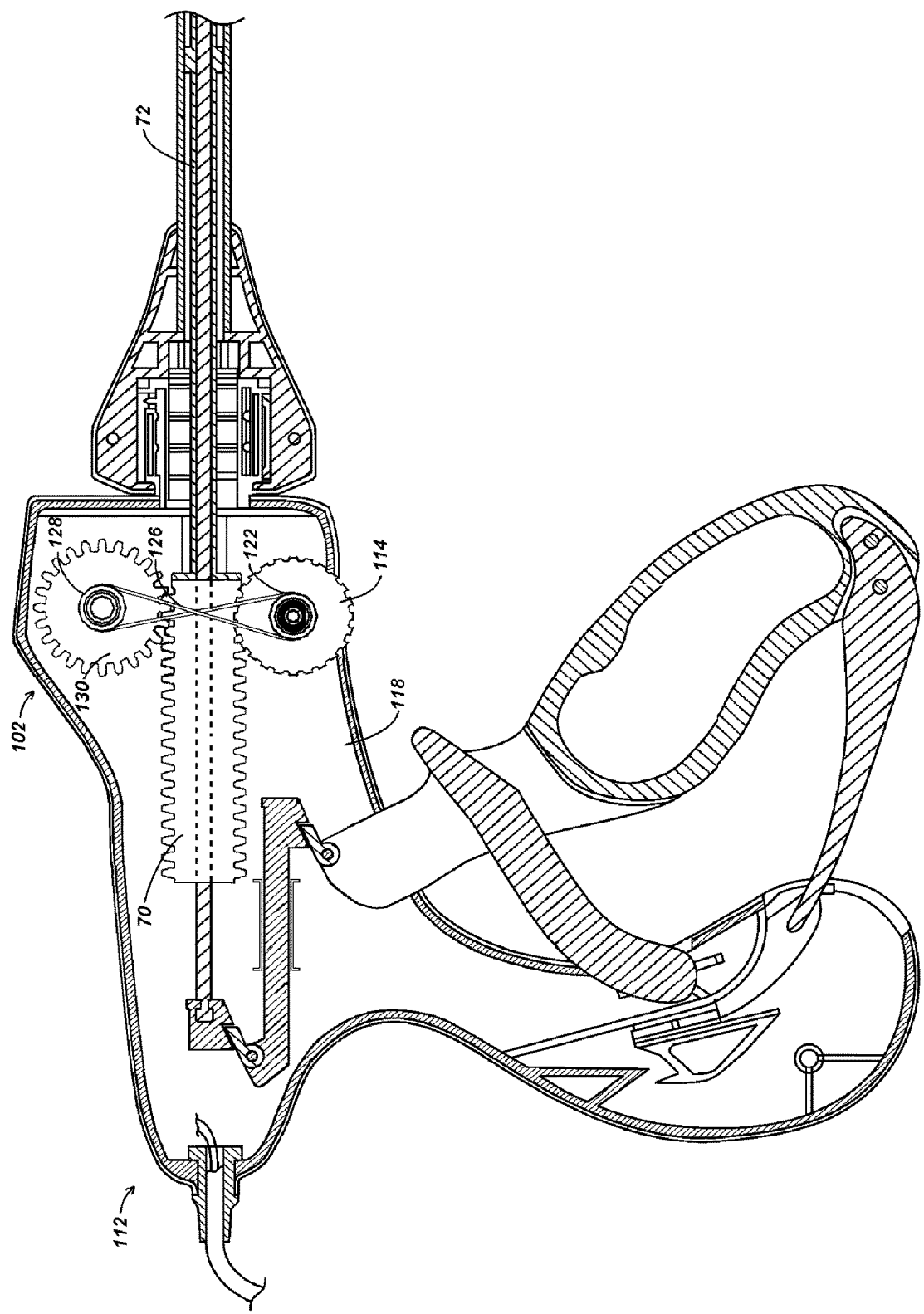
FIG. 6 is a partial, cross-sectional view of a handle assembly depicting an alternate embodiment of a drive mechanism.

Referring now to FIG. 6, an alternate embodiment of a drive mechanism 102 is housed in a handle assembly 112. Drive mechanism 102 includes a drive wheel 114 rotatably mounted to a stationary handle 118. The drive wheel 114 protrudes to an exterior of the stationary handle 118 such that the drive wheel 114 is accessible by an operator while gripping handle assembly 112. A drive pulley 122 is mounted on the drive wheel 114 to such that the drive pulley 122 rotates along with the drive wheel 114. The drive pulley 122 engages a belt 126, which extends to a follower pulley 128. The belt 126 assumes a "figure-eight" configuration such that follower pulley 128 may rotate in an opposite direction than the drive pulley 122. A standard loop configuration is also contemplated for the belt 126 wherein the follower pulley 128 and drive pulley 122 rotate in the same direction. The follower pulley 128 is mounted on an intermediate gear 130 such that the intermediate gear 130 rotates along with the follower pulley 128. The intermediate gear 130 drives rack 70, which advances knife tube 72 as described above with reference to FIG. 2A.

In use, an operator may rotate the drive wheel 114 to induce longitudinal motion in the knife tube 72. As the operator rotates drive wheel 114, drive pulley 122 rotates one revolution for each revolution of the drive wheel 114. Drive pulley 122, in turn, drives follower pulley 128. The follower pulley 128 may define a smaller circumference than the drive pulley 122 such the follower pulley 128 rotates more than one revolution for each revolution of the drive pulley 122 and drive wheel 114. The intermediate gear 130 rotates one revolution for each revolution of the follower pulley 128. Since the intermediate gear 130 defines a larger circumference than the follower pulley 128, the intermediate gear 130 may drive the rack 70 and knife tube 72 a greater longitudinal distance than a direct connection between the rack and drive wheel 114.

Although the foregoing disclosure has been described in some detail by way of illustration and example, for purposes of clarity or understanding, it will be obvious that certain changes and modifications may be practiced within the scope of the appended claims.

What is claimed is:
1. A surgical instrument, comprising:
   a housing;
   an elongate shaft extending distally from the housing;
   a pair of jaw members disposed at a distal end of the elongate shaft and configured to grasp tissue;
   a rack disposed within the housing and configured to move along a longitudinal axis, the rack having a plurality of teeth;

a drive rod disposed through the rack and configured to move at least one jaw member of the pair of jaw members;

a first gear disposed within the housing and out of contact with the rack; and a second gear concentric with the first gear and having a plurality of teeth configured to engage the plurality of teeth of the rack, wherein rotation of the first gear induces rotation of the second gear to cause movement of the rack along the longitudinal axis.

2. The surgical instrument according to claim 1, wherein the second gear is fixed relative to the first gear.

3. The surgical instrument according to claim 1, further comprising a trigger having a first portion disposed exterior to the housing and a second portion disposed within the housing, wherein the second portion is in direct contact with the first gear and configured to rotate within the housing to cause rotation of the first gear.

4. The surgical instrument according to claim 3, wherein the second portion of the trigger defines a plurality of teeth configured to engage a plurality of teeth defined by the first gear.

5. The surgical instrument according to claim 3, wherein the trigger is configured to rotate about a pivot pin disposed within the housing.

6. The surgical instrument according to claim 1, further comprising a knife tube coupled to the rack and configured to move along the longitudinal axis in response to movement of the rack along the longitudinal axis.

7. The surgical instrument according to claim 6, wherein the drive rod is configured to move longitudinally within the knife tube.

8. The surgical instrument according to claim 6, further comprising a knife coupled to a distal end portion of the knife tube and configured to move along the longitudinal axis.

9. The surgical instrument according to claim 6, wherein the knife tube is disposed distal to the rack.

10. The electrosurgical instrument according to claim 1, wherein the drive rod is configured to move relative to the rack.

11. The electrosurgical instrument according to claim 1, wherein a proximal end portion of the drive rod is disposed proximal to a proximal end of the rack.

12. A surgical instrument, comprising:

a housing;

a trigger coupled to the housing and having a first portion disposed exterior to the housing and a second portion disposed within the housing, the second portion having a plurality of teeth;

a rack disposed within the housing configured to move along a longitudinal axis;

a drive rod disposed through the rack and configured to move along the longitudinal axis;

a first gear having a plurality of teeth in direct contact with the plurality of teeth of the second portion of the trigger such that rotation of the trigger rotates the first gear; and a second gear coupled to the rack, wherein rotation of the first gear induces rotation of the second gear to move the rack along the longitudinal axis.

13. The surgical instrument according to claim 12, wherein the first and second gears are concentric.

14. The surgical instrument according to claim 12, further comprising a knife tube coupled to the rack and configured to move along the longitudinal axis in response to movement of the rack.

15. The surgical instrument according to claim 14, wherein the drive rod is configured to move longitudinally within the knife tube.

16. The surgical instrument according to claim 12, further comprising a handle configured to move relative to the housing to cause movement of the drive rod along the longitudinal axis.

17. The surgical instrument according to claim 16, wherein the trigger is configured to rotate relative to the handle and the housing to rotate the first gear.

18. The surgical instrument according to claim 12, wherein the second gear defines a plurality of teeth configured to engage a plurality of teeth defined by the rack.

19. A surgical instrument, comprising:

a housing;

a rack disposed within the housing and configured to move along a longitudinal axis;

a drive rod disposed through the rack and configured to move relative to the rack along the longitudinal axis;

a handle configured to rotate relative to the housing to move the drive rod along the longitudinal axis;

a trigger configured to rotate relative to the handle and the housing;

a first gear coupled to the trigger such that rotation of the trigger rotates the first gear; and a second gear coupled to the first gear and the rack, wherein rotation of the first gear induces rotation of the second gear to move the rack along the longitudinal axis.

20. The surgical instrument according to claim 19, wherein the first and second gears are concentric.

* * * * *